(12) United States Patent
Zhang (10) Patent No.: US 12,376,897 B2
(45) Date of Patent: Aug. 5, 2025

(54) APPARATUSES AND METHODS FOR THE CONTROL AND OPTIMIZATION OF ICE FORMATION DURING CRYOABLATION TREATMENTS

(71) Applicant: Varian Medical Systems, Inc., Palo Alto, CA (US)

(72) Inventor: Hongxuan Zhang, Austin, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 582 days.

(21) Appl. No.: 17/655,230

(22) Filed: Mar. 17, 2022

(65) Prior Publication Data

US 2023/0293219 A1    Sep. 21, 2023

(51) Int. Cl.
A61B 18/02    (2006.01)
A61B 18/00    (2006.01)

(52) U.S. Cl.
CPC .... *A61B 18/02* (2013.01); *A61B 2018/00023* (2013.01); *A61B 2018/00577* (2013.01); *A61B 2018/00666* (2013.01); *A61B 2018/00744* (2013.01); *A61B 2018/00791* (2013.01)

(58) Field of Classification Search
CPC .................................................... A61B 18/02
See application file for complete search history.

(56) References Cited

U.S. PATENT DOCUMENTS

| | | | |
|---|---|---|---|
| 6,190,378 B1 * | 2/2001 | Jarvinen | A61B 18/02 |
| | | | 606/23 |
| 7,479,139 B2 | 1/2009 | Cytron et al. | |
| 8,092,448 B2 | 1/2012 | DeLonzor | |
| 8,475,441 B2 | 7/2013 | Babkin et al. | |
| 9,078,733 B2 | 7/2015 | Ramadhyani et al. | |
| 9,956,024 B2 | 5/2018 | Mahrouche et al. | |
| 12,193,728 B2 | 1/2025 | Narayan | |
| 2004/0215295 A1* | 10/2004 | Littrup | F25D 3/10 |
| | | | 607/96 |
| 2005/0177146 A1 | 8/2005 | Sherman | |

(Continued)

FOREIGN PATENT DOCUMENTS

CN    113952021 A    1/2022
EP    3766445 A1    1/2021

(Continued)

OTHER PUBLICATIONS

International Search Report and Written Opinion for PCT/US2023/064541 issued Jun. 30, 2023, 15 pages.

(Continued)

*Primary Examiner* — Ronald Hupczey, Jr.
(74) *Attorney, Agent, or Firm* — Duane Morris LLP (57) ABSTRACT

A method of performing a cryoablation treatment may include positioning a plurality of measurement points in predetermined locations relative to a target tissue in a patient and obtaining ice formation measurement information from the plurality of measurement points. The method may also include comparing the ice formation measurement information to a predetermined ice formation plan and adjusting a flow of a cryo-fluid to a cryoprobe if the ice formation measurement information deviates from the predetermined ice formation plan by more than predetermined deviation level.

20 Claims, 9 Drawing Sheets

(56) References Cited

U.S. PATENT DOCUMENTS

| | | |
|---|---|---|
| 2006/0155267 A1* | 7/2006 | Berzak .................. A61B 18/02 606/20 |
| 2008/0027420 A1 | 1/2008 | Wang et al. |
| 2009/0292280 A1 | 11/2009 | Cytron et al. |
| 2009/0318804 A1 | 12/2009 | Avital et al. |
| 2010/0168725 A1 | 7/2010 | Babkin et al. |
| 2012/0191081 A1 | 7/2012 | Markowitz |
| 2013/0060242 A1 | 3/2013 | Babkin et al. |
| 2014/0243808 A1 | 8/2014 | Molnar-Hammond et al. |
| 2014/0330262 A1 | 11/2014 | Jannicke et al. |
| 2017/0172791 A1 | 6/2017 | Baust et al. |
| 2018/0310978 A1 | 11/2018 | Avitall |
| 2020/0107877 A1 | 4/2020 | Koblish et al. |
| 2020/0108222 A1 | 4/2020 | Bianco |
| 2021/0052314 A1 | 2/2021 | Holsing et al. |
| 2021/0290285 A1 | 9/2021 | Avitall et al. |
| 2021/0369393 A1 | 12/2021 | Braido et al. |
| 2022/0110669 A1 | 4/2022 | Chang et al. |
| 2022/0133381 A1 | 5/2022 | Prologo et al. |

FOREIGN PATENT DOCUMENTS

| | | |
|---|---|---|
| EP | 3903705 A1 | 11/2021 |
| WO | 2008112005 A1 | 9/2008 |
| WO | 2008142686 A2 | 11/2008 |
| WO | 2021007348 A1 | 1/2021 |
| WO | 2021168367 A1 | 8/2021 |
| WO | 2022251236 A1 | 12/2022 |
| WO | 2023177828 A1 | 9/2023 |
| WO | 2023178243 A1 | 9/2023 |
| WO | 2023178247 A1 | 9/2023 |
| WO | 2023178274 A1 | 9/2023 |

OTHER PUBLICATIONS

Networked Robotics Corporation. (Jun. 2020). Monitoring Liquid Nitrogen Storage Dewars by weight. https://www.networkedrobotics.com/documentation/Monitoring-Liquid-Nitrogen-Storage-Dewars-by-Weight.pdf (Year: 2020).

Golkar, E., Rao, P. P., Joskowicz, L., Gangi, A, & Essert, C. (2019). GPU-based 3D iceball modeling for fast cryoablation simulation and planning. International Journal of Computer Assisted Radiology and Surgery, 14, 1577-1588. (Year: 2019).

* cited by examiner

APPARATUSES AND METHODS FOR THE CONTROL AND OPTIMIZATION OF ICE FORMATION DURING CRYOABLATION TREATMENTS

FIELD

The present disclosure relates to apparatuses and methods for the control and optimization of ice formation during cryoablation treatments.

BACKGROUND

This section provides background information related to the present disclosure which is not necessarily prior art.

Systems and methods for providing cryoablation treatments may include cryoablation probes that are introduced at or near target tissue in a patient. A cryoablation system may include an extremely cold cryo-fluid (liquid, gas, or mixed phase) that may be passed through a probe in thermal contact with the target tissue. Heat from the tissue passes from the tissue, through the probe, and into the fluid that removes heat from the targeted tissue. This removal of heat causes tissue to freeze, resulting in the destruction of the targeted tissue. When the tissue freezes, ice forms typically in an iceball. The iceball may be in the form a sphere, ellipsoid or other rounded shape. It is desirable to perform cryoablation treatments such that the target tissue is completely frozen and that the freezing of surrounding tissues and/or body structures is minimized.

Traditional or existing systems and methods do not include elements or methods often include predetermined test procedures that are often determined experimentally in a laboratory environment. Traditional or existing systems and methods do not include the capability to accurately monitor and control the formation of ice during cryoablation treatments. As such, the ice that forms using existing and traditional methods and systems may not perform as efficiently and effectively as desired in freezing targeted tissue. Furthermore, treatments using existing and traditional methods may unnecessarily form ice that freezes healthy tissue or body structures adjacent to or surrounding the target tissue. In addition, traditional and existing systems and methods are poor at accounting for differences between treatment sites, patients, tissue, and other factors. There exists a need, therefore, for improved cryoablation systems and methods to monitor, control and adapt to the particular circumstances of each cryoablation treatment and to efficiently and effectively form ice in a desired size, shape and location.

SUMMARY

This section provides a general summary of the disclosure, and is not a comprehensive disclosure of its full scope or all of its features.

In some embodiments of the present disclosure, a cryoablation system may include a cryoablation computing device that is coupled to a cryo-fluid delivery apparatus and to one or more measurement points. The measurement points are configured to provide impedance and/or temperature measurement at one or more locations on or surrounding a cryoprobe. The measurement points provide feedback to the cryoablation computing device regarding the formation of ice. Based on the feedback from the measurement points, the cryoablation computing device can monitor, control and/or adjust one or more operating parameters of the cryo-fluid delivery apparatus to cause the ice to form according to one or more desired ice characteristics such as size, rate of growth, shape and the like. The cryoablation system can continue to monitor, control and/or adjust the operating parameters of the cryo-fluid delivery apparatus until the ice achieves a predetermined size and shape.

In some embodiments, a system for performing a cryoablation treatment is provided. The cryoablation system may include at least one computing device configured to obtain ice formation measurement information from a plurality of measurement points. The plurality of measurement points may be positioned at predetermined locations relative to a target tissue in a patient. The at least one computing device may be further configured to compare the ice formation measurement information to a predetermined ice formation plan, and adjust a flow of a cryo-fluid to a cryoprobe if the ice formation measurement information deviates from the predetermined ice formation plan by more than predetermined deviation level.

In one aspect, the plurality of measurement points may be positioned on the cryoprobe.

In another aspect, the plurality of measurement points may be positioned on a measurement lead and the measurement lead is positioned in a desired orientation relative to the cryoprobe.

In another aspect, the plurality of measurement points may be positioned on both a cryoprobe and a measurement lead.

In another aspect, the ice formation measurement information may include temperatures at the plurality of measurement points, and the at least one computing device compares the temperatures to temperature thresholds.

In another aspect, the at least one computing device may determine a rate of change of a temperature at each measurement point of the plurality of measurement points and compare each rate of change of the temperature to a temperature profile.

In another aspect, the at least one computing device may be configured to adjust at least one of a flow speed or a flow volume of the cryo-fluid flow.

In another aspect, the at least one computing device may be configured to adjust at least one of a pulse width, a pulse amplitude and a pulse frequency of the cryo-fluid flow.

In another aspect, the at least one computing device may be configured to continuously obtain the ice formation measurement information and continuously adjust the flow of the cryo-fluid to the cryoprobe if the ice formation measurement information deviates from the predetermined ice formation plan until the ice formation measurement information that a desired ice formation has been achieved for predetermined freezing time.

In another aspect, the system may also include a pump fluidly connected to a cryo-fluid source and a cryo-fluid supply line. The at least one computing device may be further configured to adjust the flow of the cryo-fluid to the cryoprobe using the pump.

In some embodiments a method of performing a cryoablation treatment is provided the method may include positioning a plurality of measurement points in predetermined locations relative to a target tissue in a patient and obtaining ice formation measurement information from the plurality of measurement points. The method may also include comparing the ice formation measurement information to a predetermined ice formation plan and adjusting a flow of a cryo-fluid to a cryoprobe if the ice formation measurement information deviates from the predetermined ice formation plan by more than predetermined deviation level.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In some embodiments of the present disclosure, a cryoablation system is provided that may include at least one computing device that can automatically obtain ice formation measurement information that characterizes the ice being formed by a cryoprobe during freezing cycle. The ice formation measurement information can be used to determine whether the ice is growing as expected according an ice formation plan. If the ice is forming to rapidly or too slowly, the flow of a cryo-fluid (e.g., liquid nitrogen) can be adjusted to either slow down or speed up the growth of the ice at the target tissue. The cryoablation system can be configured as a closed loop system to continuously, semi-continuously, or periodically monitor and control the formation of ice.

The systems and methods of the present disclosure are improvements over existing or traditional systems. Existing or traditional system often use predetermined ice formation procedures that are based on experimental or laboratory tests. These ice formation procedures often do not account for differences between patients, and patient conditions as well as differences in tissue and body structures of patients. Thus, existing and traditional systems do not actively adjust or control operating parameters of the cryo-fluid in real-time during a cryoablation treatment.

In addition, existing and traditional systems do not include structures or equipment that are configured to collect ice formation measurement information during cryoablation treatments. Imaging systems such as ultrasound device, CT scan devices, x-ray device, and/or MRI devices may be used but such devices are poor at delivering real-time and/or accurate information regarding ice formation during treatment.

The systems and methods of the present disclosure are improvements over traditional and existing systems by having measurement points configured and located on a cryoprobe and/or on a measurement lead to provide ice formation measurement information that can accurately and repeatably provide ice formation measurement information so that the growth of ice at the target tissue is known and can be used to adjust the growth of ice, if necessary. The systems and methods of the present disclosure can improve the efficiency and effectiveness of the cryoablation treatments by providing ice formations as desired to destroy the target issue with reduced and/or minimized harm to healthy tissue.

The cryoablation systems of the present disclosure may also use one or more elements or methods as described in U.S. patent application Ser. No. 17/697,216 entitled "APPARATUSES AND METHODS FOR ADAPTIVELY CONTROLLING CRYOABLATION SYSTEMS" filed on the same day as the present application by Varian Medical Systems, Inc., U.S. patent application Ser. No. 17/655,204 entitled "APPARATUSES AND METHODS FOR SEQUENTIAL HEATING OF CRYO-FLUID IN CRYOABLATION SYSTEMS" filed on the same day as the present application by Varian Medical Systems, Inc., and U.S. patent application Ser. No. 17/655,218 entitled "APPARATUSES AND METHODS FOR MONITORING AND CONTROLLING BLEEDING DURING CRYOABLATION TREATMENTS" filed on the same day as the present application by Varian Medical Systems, Inc.

Figure 1:
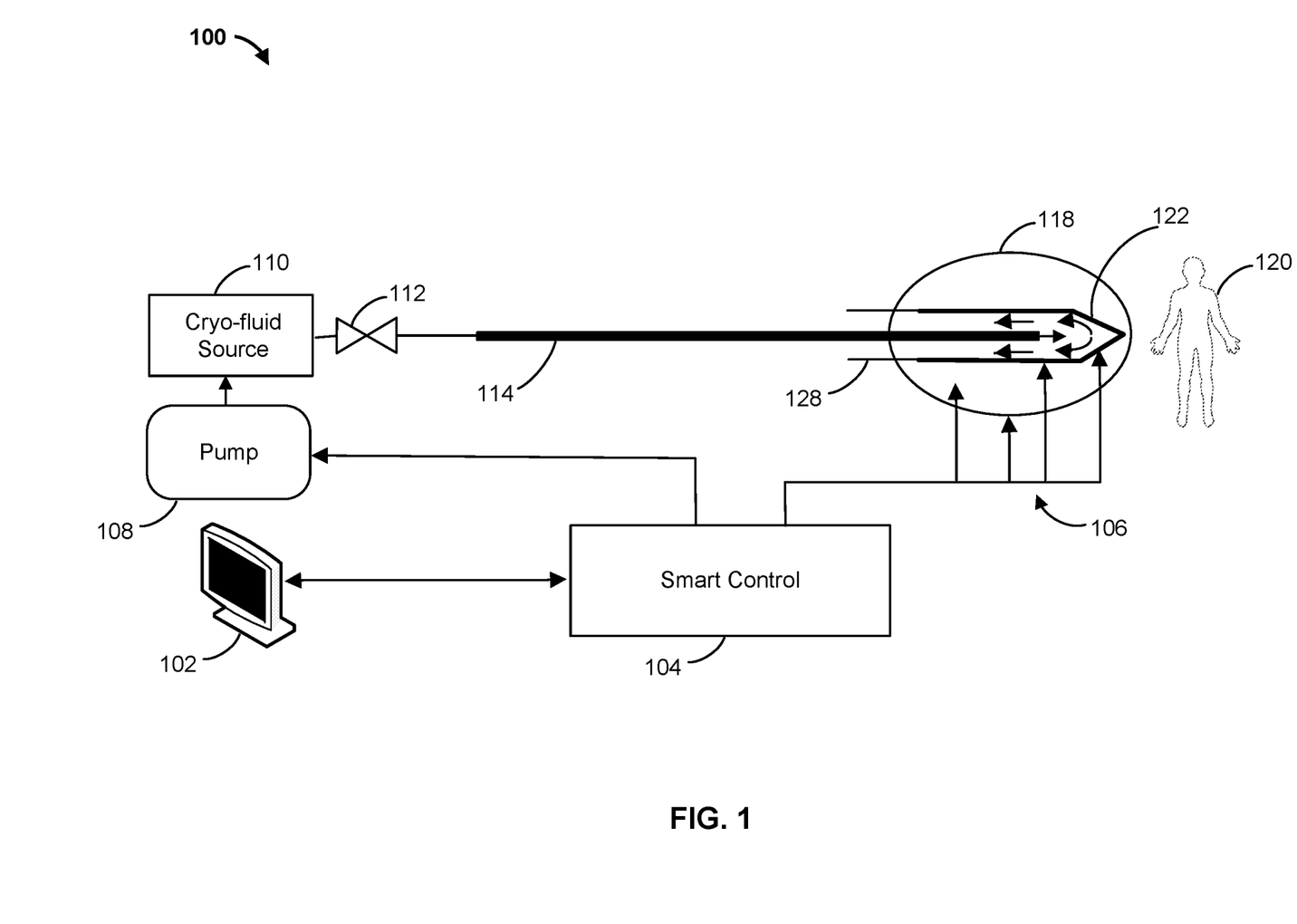
FIG. 1 is a diagram illustrating an example cryoablation system in accordance with some embodiments of the present disclosure.

Referring now to FIG. 1, an example cryoablation system 100 is shown. The cryoablation system 100 may include a cryoablation computing device 102, a smart control 104, a plurality of measurement points 106, a pump 108, a cryo-fluid source 110, an inlet valve 112, a cryo-fluid supply 114, and a cryoprobe 128. The pump 108, the cryo-fluid source 110, the inlet valve 112, the cryo-fluid supply 114, and the cryoprobe 128 may operate to deliver a cryo-fluid from the cryo-fluid source 110 to the cryoprobe 128 to perform a cryoablation treatment. The cryo-fluid (e.g., liquid nitrogen) can be stored in the cryo-fluid source 110, such as a dewar or other suitable container, and then delivered to the cryoprobe 128 via the cryo-fluid supply 114. The cryo-fluid may expand at a tip 122 of the cryoprobe 128 and cool the tip 122 of the cryoprobe 128 to a temperature at which the target tissue of a patient 120 begins to freeze forming an iceball.

The cryoprobe 128 can be positioned at or near a target tissue (e.g., a tumor) in the patient 120. In this manner, the target tissue can be frozen destroying the target tissue. One or more freezing cycles can be performed in order to destroy the target tissue. An iceball 118 may form at the target tissue in the patient 120 during the freezing cycle. It is desirable to control and form the iceball 118 in a predetermined manner so the iceball 118 forms to a desired size, shape and rate so that the target tissue is frozen in the iceball 118 for a desired period of time. It is also desirable to form the iceball 118 with the desired size, shape and rate so that healthy tissue or body structures near the target tissue are not harmed by the freezing cycle. It can be desirable, for example, to limit a size of the iceball 118 so that it does not form and freeze healthy tissue.

A treatment plan can be determined prior to the performance of the cryoablation treatment. The treatment plan can detail and/or describe the various steps of the process and various aspects of the treatment such as the types of equipment to be used, a positioning of the cryoprobe, temperatures of the cryoprobe, duration of freezing (and thaw cycles) as well as a quantity of cycles. The treatment plan may also include a size, location, shape, growth rate and duration of an iceball. The treatment plan may be determined by a medical professional and/or by others. In some examples, the cryoablation computing device 102 may determine or recommend a treatment plan after health, patient, and other information is input into the cryoablation computing device 102 or such information is retrieved or otherwise obtained by the cryoablation computing device 102. The cryoablation computing device 102 may any suitable computing device such as a workstation, computer, laptop, tablet, server or the like.

As further shown, the cryoablation system 100 includes the smart control 104 that may be coupled to the cryoablation computing device 102, to the measurement points 106 and to the pump 108. The smart control 104 may be any suitable controller, PLC, data acquisition unit, control unit or the like that can perform the operations described herein. The smart control 104 may operate to obtain ice formation measurement information from the measurement points 106. The measurement points 106 are suitable sensors, measurement locations, or the like that can obtain ice formation measurement information from locations on or near the tip 122 of the cryoprobe 128. The ice formation measurement information may provide temperature information at predetermined locations in order to provide information regarding the growth of the ice at the target tissue. As will be further described, the measurement point may include temperature sensors, thermocouples, thermistors, impedance sensors, and the like. Such measurement points may be incorporated into the cryoprobe 128 and/or into a separate measurement lead.

The smart control 104 may operate to obtain the ice formation measurement information from the measurement points 106 and provide the information to the cryoablation computing device 102. The cryoablation computing device 102 may then perform various operations to determine characteristics of the ice being formed during a cryoablation treatment.

After determining characteristics of the ice, the cryoablation computing device 102 may take action to adjust, change, modify or otherwise control the one or more operating parameters of the cryoablation system 100. In some examples, the cryoablation computing device 102 may adjust the flow of the cryo-fluid provided from the cryo-fluid source 110 to the cryoprobe 128. The cryoablation computing device 102 may be coupled to the pump 108. The pump 108 can be an adjustable, programmable, or otherwise controllable pump. The pump 108 may allow for the flow rate, flow volume, flow speed, pressure or other characteristic of the flow of cryo-fluid to be modified, controlled or customized. In some examples, the pump 108 can operate to deliver the cryo-fluid to the cryoprobe 128 in a pulsed manner using pulse width modulation (PWM). In such examples, the pump 108 can be controlled to deliver a flow of cryo-fluid at a desired frequency, pulse width, pulse amplitude or other desired flow characteristic.

Figure 2:
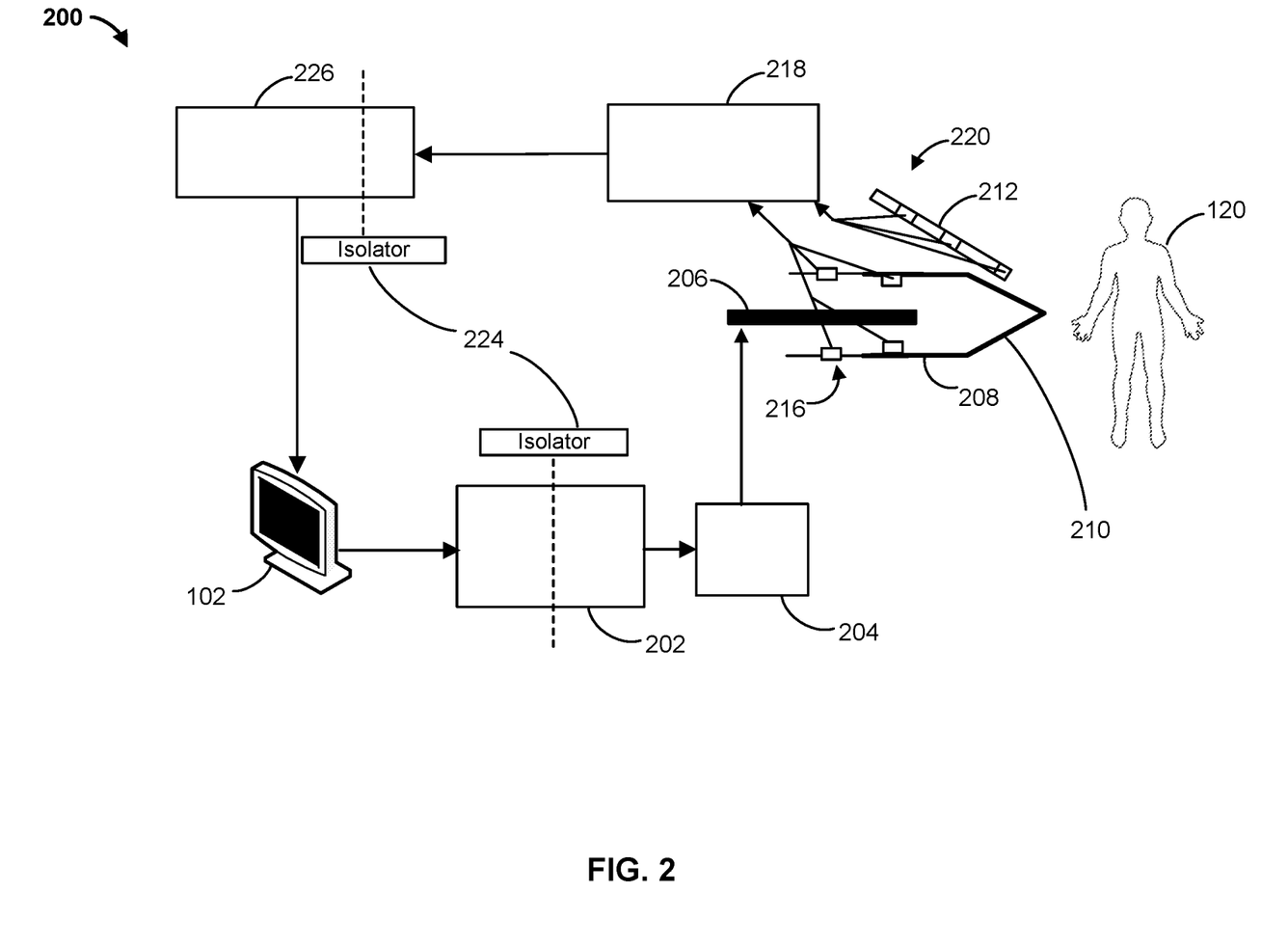
FIG. 2 is a diagram illustrating another example cryoablation system in accordance with some embodiments of the present disclosure.

Referring now to FIG. 2, an example cryoablation system 200 is shown. The cryoablation system 200 may include the cryoablation computing device 102. The cryoablation computing device may be coupled to a pump control 202 that, in turn, can be coupled to a pump 204. The pump 204 can be fluidly connected to a cryo-fluid supply 206 that can deliver the cryo-fluid to the cryoprobe 208. While not shown, the cryoablation system 200 may include other elements such as a dewar, heaters, valves, vaporizers, exhausts or the like that can be used to provide perform cryoablation treatments. The pump control 202 can include a medical power supply and/or a suitable controller to control the pump 204 and deliver the cryo-fluid using controllable and adjustable flow characteristics as previously described with respect to cryoablation system 100.

The cryoablation computing device 102 may also be coupled to the ice formation engine 226 and/or to the measurement collector 218. The measurement collector 218 can be a suitable data acquisition unit, measurement bus, or other device through which the signals from the various measurement points 216 and 212. The measurement collector 218 may obtain temperature, impedance or other signals from the measurement points 212, 216 and provide such information to the ice formation engine 226.

The ice formation engine 226 can obtain the ice formation measurement information and perform comparisons, analysis and other operations to determine if the ice that is forming during a freezing cycle of a cryoablation treatment is formed in a desired manner. The ice formation engine 226 can compare the ice formation measurement information to predetermined thresholds, to predetermined ranges, to desired ice formation growth profiles, and the like. In other examples, the ice formation engine 226 may include ice formation models or other information that characterizes a relationship between the ice formation measurement information and desired characteristics of the iceball such as a size, shape, location, growth rate and the like.

The ice formation engine 226 may obtain ice formation characteristics, ice formation models, ice formation thresholds, ice formation ranges, ice formation profiles and other information from databases, health information systems or other data sources that may be coupled to the cryoablation system 200. In the example shown, the ice formation engine 226 is shown separate from the cryoablation computing device 102. In other examples, the ice formation engine 226 may be combined as part of the cryoablation computing device 102. As can be appreciated, other aspects of the cryoablation system 100 may be combined as well but are shown separately in FIG. 2.

The cryoablation system 200 may also include isolators 224. Isolators 224 may be isolators as described in a testing standard such as the International Electrotechnical Commission (IEC) IEC60601 standard that requires patient and medical equipment isolation between main power to patient and floating ground (GND). The isolators are for patient and equipment current leakage (such as earth, enclosure, etc.). The cryoablation system may be classified as a Body Floating (BF) part for patient current requirements. The isolators 206, 220 may be a transformer or medical graded power supply that is certified by an IEC testing facility.

In the example shown, the measurement points 212 are located on a measurement lead 220. The measurement lead 220 can be a needle, probe, or other elongated device that can inserted or otherwise positioned at or near the tip 210 of the cryoprobe 208. The measurement lead 220 can include various measurement points 212 positioned at different axial or longitudinal positions along a length of the measurement lead 220. The measurement lead 220 can be positioned at a predetermined or known position and/or orientation with respect to the cryoprobe 208 and/or the target tissue in the patient 120. Since the position of the measurement lead 220 is known, information such as temperatures at various positions in the target tissue can be collected to understand the growth of ice during a cryoablation treatment.

Each of the measurement points 212 can be configured as a band, patch, strip or other piece metal isolated from adjacent or other measurement points on the measurement lead. In some instances, the measurement collector 218 can obtain an impedance of each measurement point 212. In other examples, the measurement collector can obtain a voltage at each measurement point 212. In still other examples, other measurements or signals can be obtained.

The measurement points 216 can be positioned on the cryoprobe 208. As shown, the measurement points 216 can be positioned on an external surface of the shell of the cryoprobe 208. In other examples, the measurement points can be positioned on an internal surface of the cryoprobe 208. The measurement points 216 can be configured as a band, patch, strip or other piece metal isolated from adjacent or other measurement points on the cryoprobe 208. In some instances, the measurement collector 218 can obtain an impedance of each measurement point 216. In other examples, the measurement collector can obtain a voltage at each measurement point 216. In still other examples, other measurements or signals can be obtained.

Figure 3:
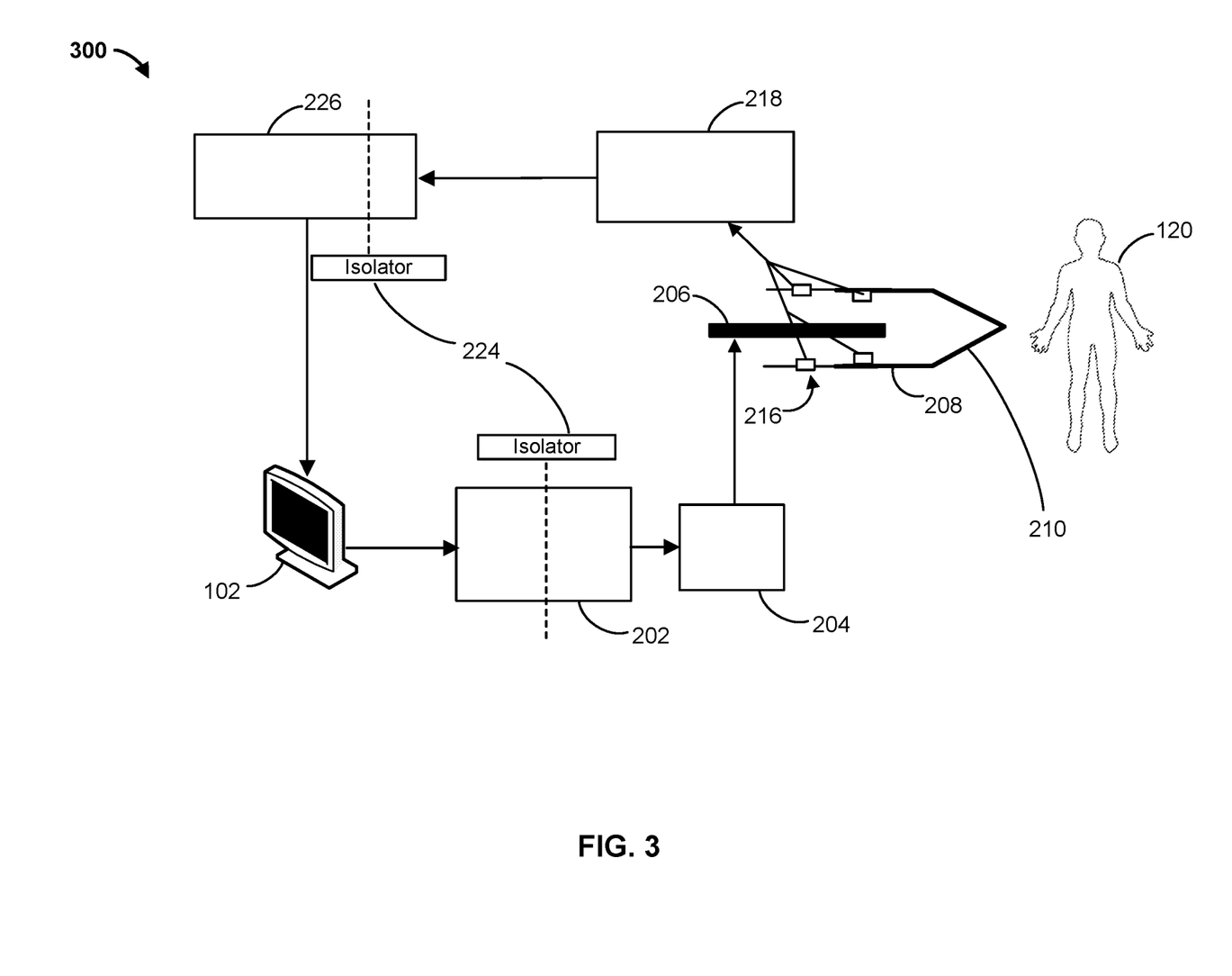
FIG. 3 is a diagram illustrating a variation of the example cryoablation system of FIG. 2.

Turning now to FIG. 3, another example cryoablation system 300 is shown. The cryoablation system 300 can be substantially the same as the cryoablation system 200 previously described. In this example, however, the cryoablation system 300 does not include the measurement lead 220. In this example, the ice formation measurement information is collected only using the cryoprobe 208 that is equipped with various measurement points 216. While only four measurement points 216 are shown, the cryoprobe 208 can be equipped with more than four measurement points 216 to collect ice formation measurement information. In still further examples, cryoablation systems 200 may include measurement points that are only positioned on a measurement lead, such as measurement lead 220. Such systems can be used in connection with traditional or existing cryoprobes. Such traditional cryoprobes may not be equipped or may not include measurement points such as measurement points 216. In such instances, a cryoablation system can be configured similarly to the system shown in FIG. 2 but one or more measurement leads 220 can be used and the cryoprobe 208 may not include measurement points 216.

Figure 4:
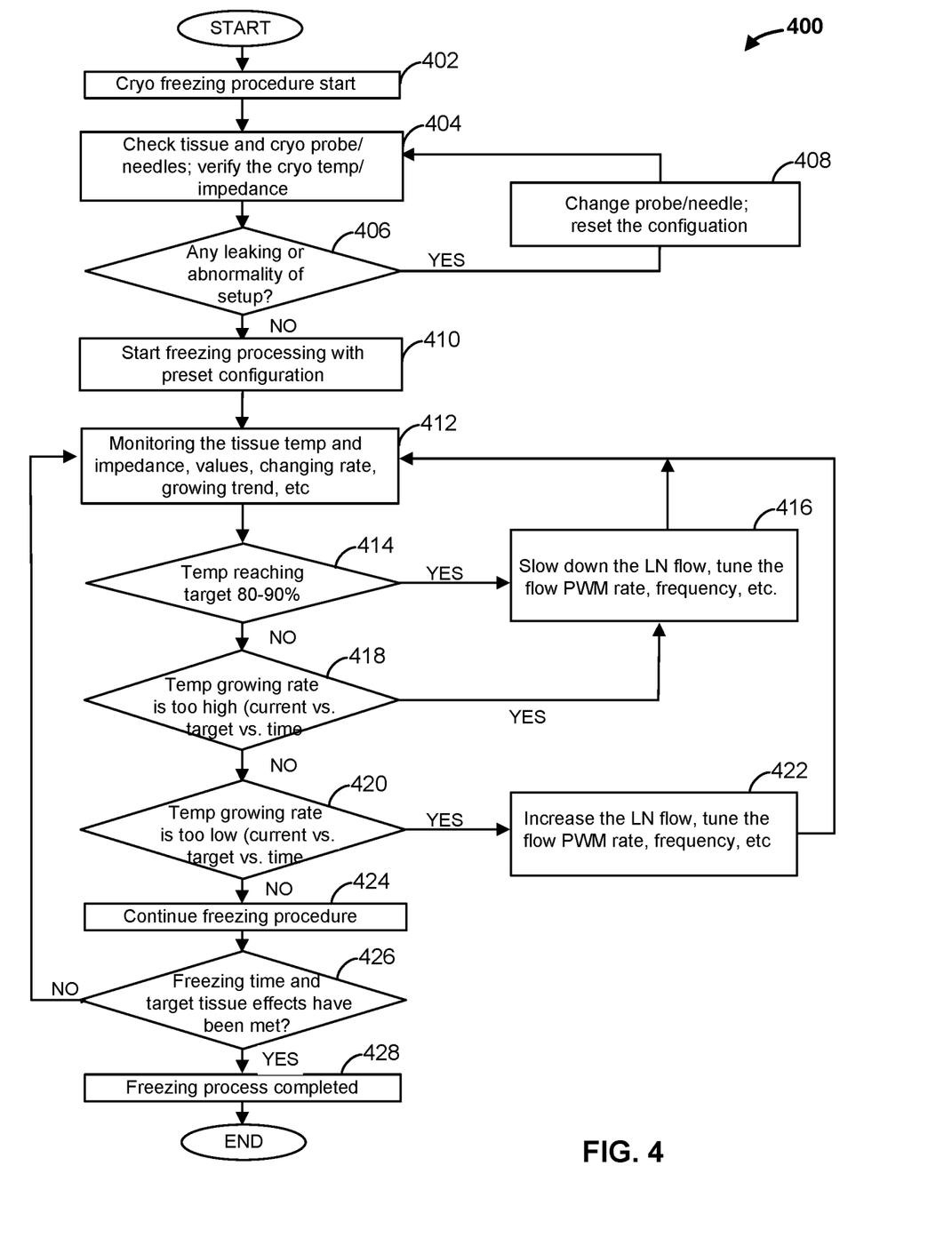
FIG. 4 is a flow chart illustrating an example method of performing a cryoablation treatment in accordance with some embodiments of the present disclosure.

FIG. 4 illustrates an example cryoablation method 400. The method 400 may be performed using one or more of the cryoablation systems described herein such as cryoablation system 100, 200 or 300. For the sake of brevity, the method 400 is described with reference to cryoablation system 200. It should be appreciated, however, that other cryoablation systems can also be used.

At step 402, the cryo freezing procedure may begin. At step 404, the cryoablation computing device 102 may check various aspects of the cryoablation system 200 to verify that the system is ready for a freezing cycle. For example, the cryoablation computing device may check the measurement lead 220 and/or the cryoprobe 208 to verify that the measurement lead 220 and/or the cryoprobe 208 is positioned in a desired position relative to a target tissue in the patient 120.

Such verification process may be performed, for example, by verifying positions using image data from a suitable imaging device such as an x-ray device, CT scan device, MRI device, ultrasound device or the like. The temperatures of the various measurement points 212, 216 can also be checked. The temperatures at the various measurement points can be compared to expected temperature thresholds and/or to expected temperature ranges.

While not shown in FIG. 4, the cryoablation computing device 102 may obtain a treatment plan from a database, health information source or other information repository. In other examples, a user or medical professional may input the treatment plan into the cryoablation computing device 102 using a user interface. The treatment plan may describe the cryoablation treatment including various parameters, settings and other information regarding the treatment. The treatment plan may include an ice formation plan that details the characteristics of the desired iceball including a size, shape, temperature, growth rate, location and the like. The treatment plan may include predetermined temperature thresholds, temperature ranges and/or temperature profiles. The treatment plan may also include ice formation growth rate thresholds, ranges and other information that may be used by the cryoablation computing device 102.

At step 406, the cryoablation computing device 102 determines whether there is any leaking or abnormality with the initial settings, operation or location of the various elements of the cryoablation system 200. If the cryoablation computing device 102, determines that there is leaking or abnormality, the method 400 proceeds to step 408. At step 408, the cryoprobe 208, the measurement lead 220 can be repositioned or replaced. Other remedial actions may also be taken as may be required to address any abnormalities detected during steps 404 and 406. After step 408, the cryoablation computing device 102 may repeat steps 404 and 406 until no leakage or abnormalities are detected.

If the cryoablation computing device 102 determines that there is no leakage and/or abnormalities with the setup of the cryoablation system 200, the method 400 can proceed to step 410. At step 410, the freezing cycle can be initiated by the cryoablation computing device 102. The cryoablation computing device 102 may initiate the flow of the cryo-fluid to the cryoprobe 208 using a preset configuration. The treatment plan may, for example, describe an initial configuration and may describe the initial operating conditions. The settings may include a flow rate, pressure, temperature, pulse profile or the like for the flow of cryo-fluid to the cryoprobe 208. The cryoablation computing device 102 may send instructions to the pump control 202 and/or to the pump 204 to initiate the freezing cycle using such initial or preset conditions.

At step 412, the cryoablation computing device 102 can monitor the conditions of ice formation at the target tissue. The cryoablation computing device 102 can receive ice formation measurement information from the measurement points 212, 216. The ice formation measurement information may include, for example, temperatures at the measurement points 212, 216. The cryoablation computing device 102 may also receive ice formation measurement information periodically, semi-continuously or continuously over time to determine a growth or growth rate of the ice at the target tissue.

At step 414, the cryoablation computing device 102 may determine whether the temperature at one or more of the measurement points 212, 216 has reached a predetermined temperature threshold and/or falls within a predetermined temperature range. In one example, the cryoablation computing device 102 may determine whether the temperature at one or more of the measurement points 212, 216 has reached 80-90% of a predetermined target temperature. It may be desirable to determine such information because of thermal momentum in the freezing cycle. It can be desirable to stop a freezing cycle at 80-90% of a target because once the flow of cryo-fluid (or other active cooling) is stopped, ice may continue to form for a period of time. Thus, the cryo-fluid flow can be stopped at 80-90% of a target and still achieve the target temperature and target ice formation. In other examples, other levels other than 80-90% can be used such as 75-85%, 75-90%, 85-95%, 85-90% or other ranges.

If the cryoablation computing device 102 determines that the temperature has reached the desired temperature range, the method 400 may continue to step 416. At step 416, the cryoablation computing device 102 may slow down the flow of the cryo-fluid or otherwise tune or adjust the flow the cryo-fluid. The cryoablation computing device 102 may, for example, send instructions to the pump control 202 and/or to the pump 204 to change a flow speed, flow volume, flow rate, pressure, pulse width pulse amplitude, pulse frequency or other flow characteristic.

If the cryoablation computing device 102 determines that the temperature at the measurement point has not reached the predetermined temperature threshold or range, the method 400 may proceed to step 418. At step 418, the cryoablation computing device 102 may determine, for any of the locations associated with the measurement points 212, 216, whether a temperature growth rate is too high. Such determination can be made, for example, by comparing a rate of change of the temperature at the measurement point is greater than or equal to a predetermined growth rate threshold or falls with a predetermined growth rate range. If the cryoablation computing device 102 determines that the temperature growth rate is too high (e.g., is greater than a predetermined growth rate threshold), the method may proceed to step 416 and the cryoablation computing device may adjust, change and/or slow the flow of the cryo-fluid as previously described and then return to step 412.

If the cryoablation computing device 102 determines that the temperature growth rate is not too high, the method 400 may proceed to step 420. At step 420, the cryoablation computing device 102 may determine whether the temperature growth rate at one or more of the locations associated with the measurement points 212, 216 is too low. The cryoablation computing device 102 may make such determination in a similar manner to that described above at step 418 except the cryoablation computing device 102 may determine whether the temperature growth rate is at or below a predetermined growth rate threshold.

If the cryoablation computing device 102 determines that a temperature growth rate is too low, the method may proceed to step 422. At step 422, the cryoablation computing device 102 may take action to increase, adjust, modify or otherwise change the flow of the cryo-fluid. The cryoablation computing device 102 may change a flow speed, flow volume, flow rate, pressure, pulse width pulse amplitude, pulse frequency or other flow characteristic.

If the cryoablation computing device 102 determines that none of the temperature growth rates are too low, the method 400 may proceed to step 424. At step 424, the cryoablation computing device 102 may continue to operate the cryoablation system 100 under the current settings since the ice formation measurement information indicates that the ice is forming at a desired manner in accordance with the treatment plan.

At step 425, the cryoablation computing device 102 may determine whether the freezing cycle and ice formation has been performed for a desired time and location. The cryoablation computing device 102 may monitor a duration of the freezing cycle in time and may monitor a duration based on one or more events such as a size, location, temperature or other event that may occur during the freezing cycle. The durations may be predetermined and may be described in the treatment plan. Freezing cycle durations and other event information may vary according to the type of the target tissue and/or according to a location of the target tissue in the patient 120, for example.

If the cryoablation computing device 102 determines that the freezing cycle duration and/or other cycle requirements have not been achieved, the method return to step 412 to re-perform the steps 412 through 426 as previously described. In this manner, the cryoablation computing device 102 can continuously, semi-continuously or periodically monitor the performance of the freezing cycle, including the formation of the iceball, and make adjustments or changes as required in order to form the iceball at a desired size, location, shape, temperature and duration.

If the cryoablation computing device 102 determines that the freezing cycle duration and/or other cycle requirements have been achieved, the method may proceed to step 428 at which time the freezing cycle is completed and the method may end.

Figure 5:
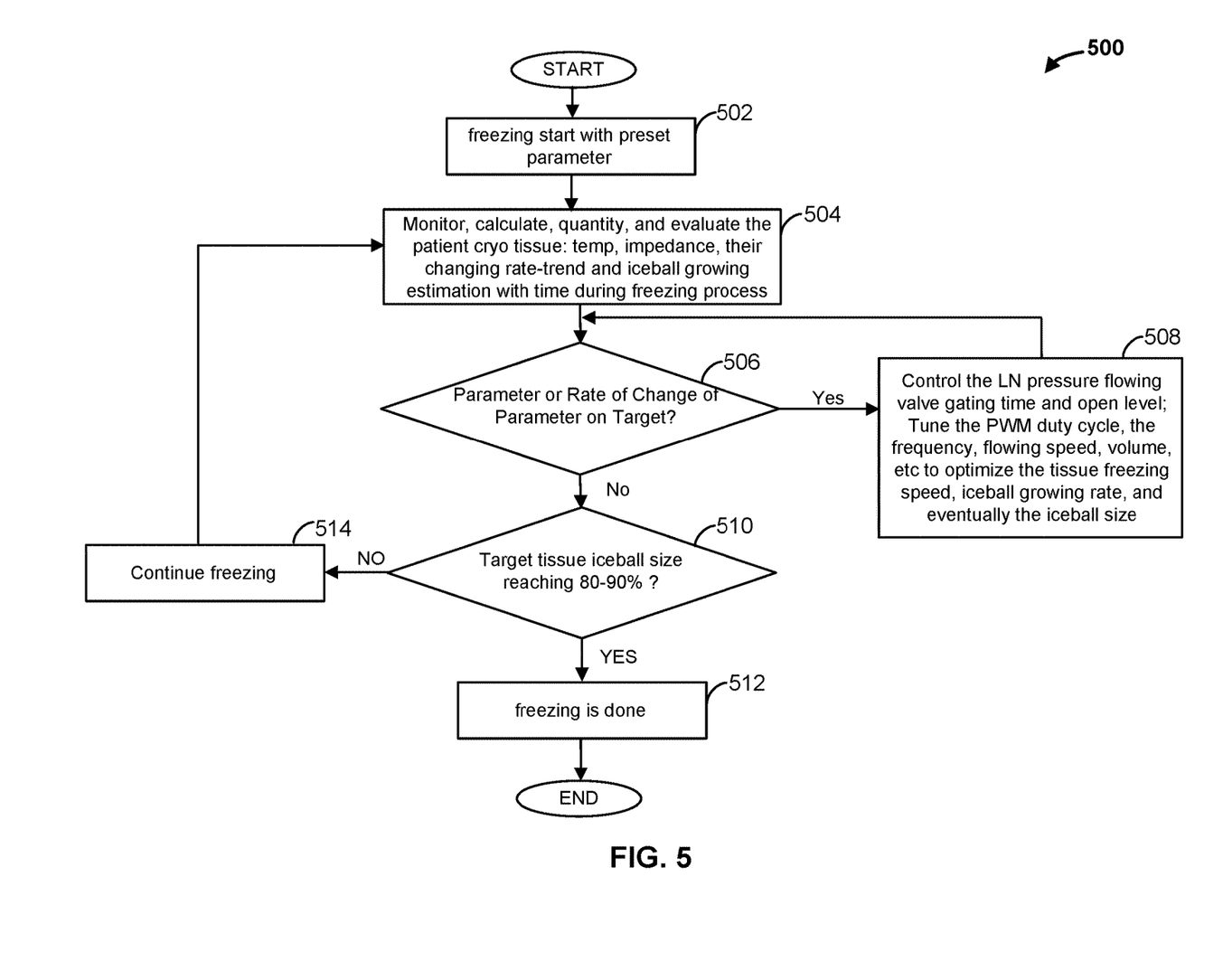
FIG. 5 is a flow chart illustrating another example method of performing a cryoablation treatment in accordance with some embodiments of the present disclosure.

Referring now to FIG. 5, another example method 500 of performing a cryoablation treatment is shown. The method 500 may be performed using one of the cryoablation systems of the present disclosure such as cryoablation system 100, 200 or 300. For the sake of brevity, the method 500 is described with reference to the cryoablation system 200 but it should be appreciated that other cryoablation systems can also be used.

At step 502, the freezing process may be initiated using preset operating parameters. The cryoablation computing device 102 may obtain a treatment plan that contains such initial operating parameters or the parameters may be input into the cryoablation computing device 102 by a user or medical professional. The preset operating parameters may describe an initial flow of the cryo-fluid.

At step 504, the cryoablation computing device 102 may monitor the ice formation measurement information that is obtained from the measurement points 212, 216. The signals provided by the measurement points 212, 216 may include temperature signals, impedance signals, voltage signals, current signals, or other signals. These signals may be used to determine various conditions regarding the tissue and ice that forms at the target tissue. This ice formation measurement information can be collected over time to determine rates of change for the various conditions at the target tissue and the ice forming.

At step 506, the cryoablation computing device 102 may determine whether any parameter and/or a rate of change of the parameter (e.g., temperature, impedance, etc.) is on target. The cryoablation computing device 102 may make this determination by comparing parameter values to predetermined parameter thresholds, predetermined parameter ranges, and/or to predetermined parameter profiles. The predetermined parameter values, thresholds and/or profiles may described in the treatment plan or may be obtained by the cryoablation computing device from a database, health information source or other repository.

If the cryoablation computing device 102 determines that a parameter or a rate of change of a parameter is not on target, the method 500 may proceed to step 508. At step 508, the cryoablation computing device 102 may take action to change a flow of the cryo-fluid to achieve the target parameter. The cryoablation computing device 102 may, for example, change, adjust, modify, or otherwise control the cryoablation system 100 including controlling a valve gating time, controlling pump 204 or pressure. The cryoablation computing device 102 may for example, adjust a flow of the cryo-fluid such as a flow rate, flow volume, flow speed, temperature, pressure, pulse width, pulse amplitude, pulse frequency or the like. After such adjustment, the method 500 may return to step 506 to continue the process of monitoring parameters and controlling the flow of cryo-fluid.

If the cryoablation computing device 102 determines that the parameters and/or the rate of change of the parameters are on target, the method 500 proceeds to step 510. At step 510, the cryoablation computing device 102 may determine whether the iceball size has achieved a predetermined target threshold. In some examples, the target threshold is 80-90% of a final iceball size. In other examples, different predetermined target threshold can be used.

If the cryoablation computing device 102 determines that the iceball size has not achieved the predetermined target threshold, the method 500 returns to step 504 to continue the performance of steps 504 through 510. In such a manner, the cryoablation computing device 102 can continue to monitor and control the parameters of the cryoablation system 100 to form ice as prescribed in the treatment plan.

If the cryoablation computing device 102 determines that the iceball size has achieved the predetermined target threshold, the method 500 proceeds to step 512. At step 512, the freezing process is complete and the cryoablation computing device 102 may end the freezing cycle.

Figure 6:
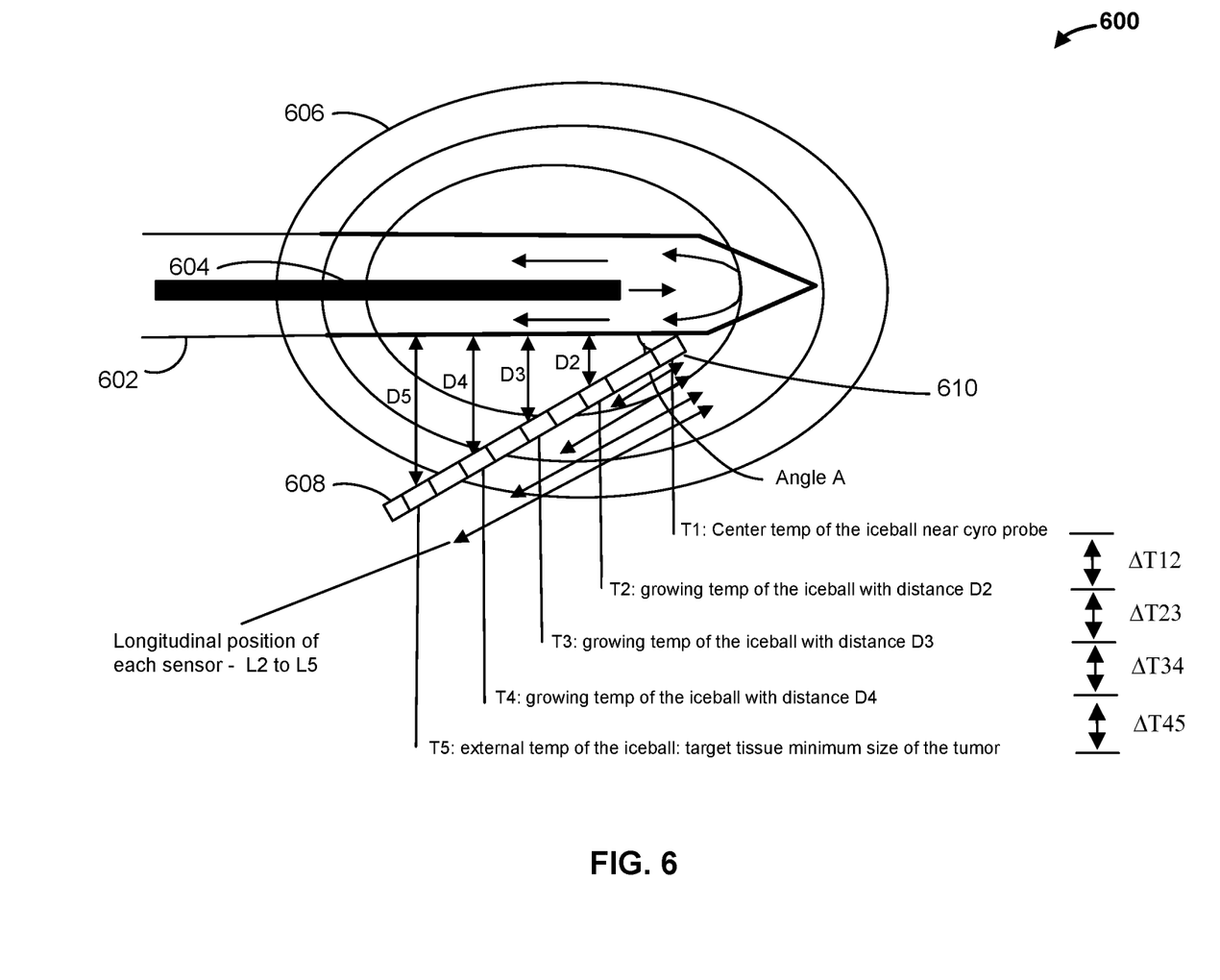
FIG. 6 is diagram illustrating an example measurement lead used to measure one or more characteristics of an ice formation in accordance with some embodiments of the present disclosure.

Referring now to FIG. 6, an example setup 600 is shown. In the cryoablation setup 600, a traditional cryoprobe 602 is used. The cryoprobe 602, in this example, does not include measurement points 216 as shown in FIGS. 2 and 3. It should be appreciated that a cryoprobe 602 that includes measurement points can alternative be used. In this example, a measurement lead 608 is positioned in a predetermined orientation relative to the cryoprobe 602.

The measurement lead 608 is positioned with a first end 610 positioned at or near a surface of the cryoprobe at a predetermined axial location along the axis of the cryoprobe 602. The measurement lead 608 is oriented at an angle A relative to the surface of the cryoprobe 602. The measurement lead 608 extends away from the first end 610 in a longitudinal direction so that the orthogonal distance of the measurement lead 608 from the surface of the cryoprobe 602 increases in a direction away from the tip of the cryoprobe 602.

Each measurement point on the measurement lead 608 is spaced apart from neighboring measurement points along the longitudinal length of the measurement lead by a distance L2 to L5. Since the angle A and the lengths L2 to L5 are known, the distances of the measurement points from the cryoprobe 602 can be determined and are shown as D2, D3, D4, D5. Each of the measurement points can operate as a sensor to measure a temperature. Each difference in temperature between adjacent measurement points can also be determined. The difference between the temperature at the first measurement point and the second measurement point is denoted as $\Delta T12$. The difference between the temperature at the second measurement point and the third measurement point is denoted as $\Delta T23$. The difference between the temperature at the third measurement point and the fourth measurement point is denoted as $\Delta T34$. The difference between the temperature at the fourth measurement point and the fifth measurement point is denoted as ΔT45. In other examples, the measurement lead 608 may include more or less than five measurement points.

With the setup 600 as shown, a size, shape and growth the iceball 606 can be determined. When the cryo-fluid is passed through the cryo-fluid supply 604 and expands in the tip of the cryoprobe 602, the temperature of the cryoprobe 602 can significantly drop that can cause ice to form around the tip of the cryoprobe 602. The iceball that forms can include one or more isotherms forming a temperature gradient that extends outward from a center of the iceball to its outer surface. The temperature gradient can be measured by the measurement points positioned at the predetermined locations relative to the cryoprobe 602 as shown.

The cryoablation computing device 102 can obtain the temperature measurements as shown and take action to adjust the flow of the cryo-fluid through the cryo-fluid supply 604 to change the rate of growth and/or size/shape of the iceball 606.

Figure 7:
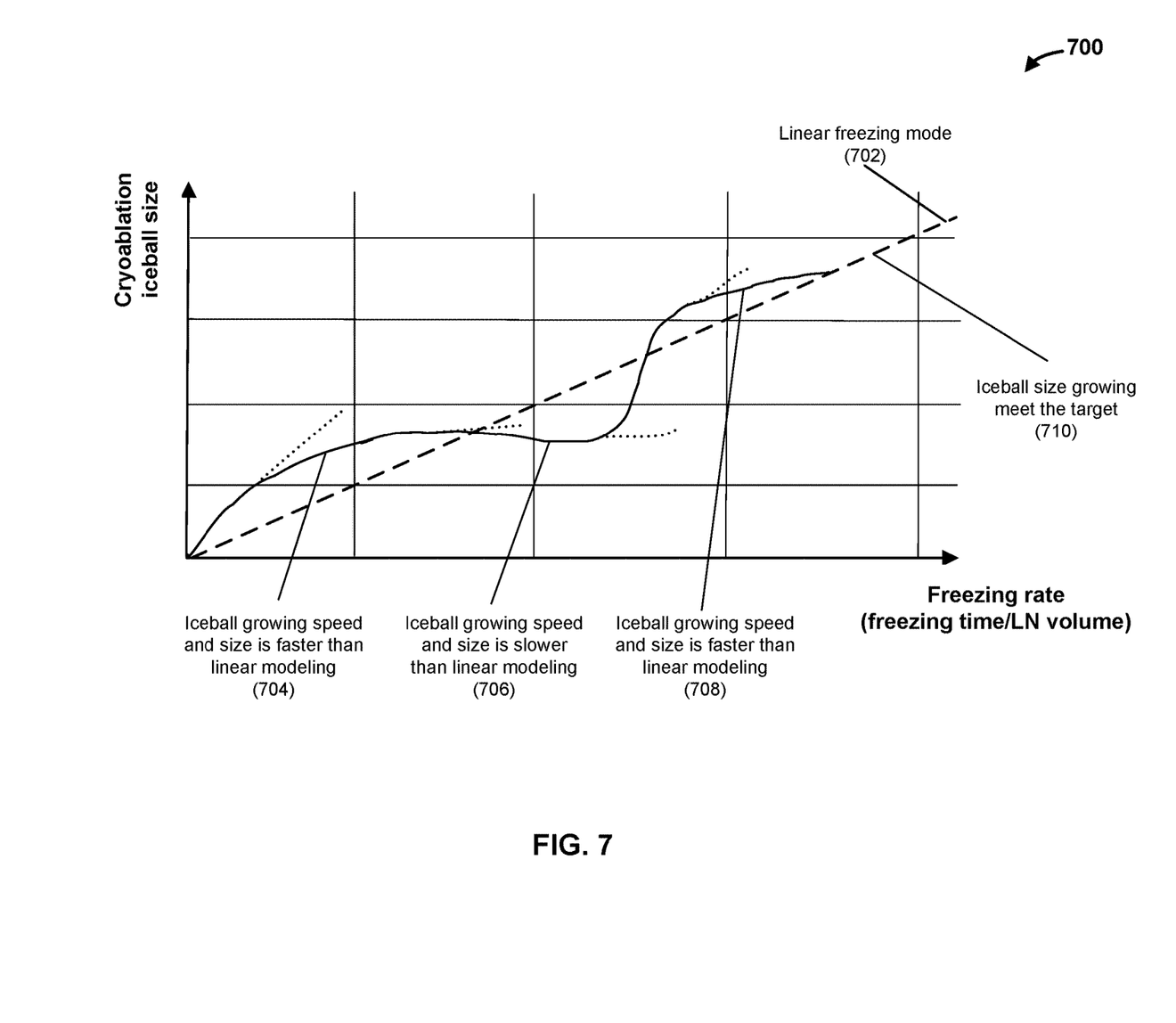
FIG. 7 is a graph of an ice formation growth profile illustrating ice formation growth versus a linear grow profile.

As shown in FIG. 7, the setup 600 or other measurement setups as described herein can be used to measure and/or monitor the formation of ice during a cryoablation treatment by tracking ice formation measurement information. As shown, a size of the iceball (e.g., diameter, length, height, etc.) can measured and plotted a function of the freezing rate (e.g., freezing time/cryo-fluid volume). The graph 700 shows an example of the iceball growth plot as compared to an ice formation profile 702. In this example, the ice formation profile 702 (dashed line) is a linear freezing mode profile. The plot shows that the growth of the iceball may vary from the ice formation profile 702. In some examples, the cryoablation computing device 102 may display a graph such as graph 700 during performance of a cryoablation treatment. In further examples, the cryoablation computing device 102 may compare the actual ice growth to the ice formation profile 702 and take action when the ice growth deviates from the ice formation profile by more than a predetermined deviation value.

For example, at portion 704 of graph 700, the ice growth indicates that the iceball growing speed is faster than the linear ice formation profile 702. In such instances, the cryoablation computing device 102 may reduce or otherwise adjust the flow the cryo-fluid to slow the ice growth. At portion 706 of graph 700, the ice growth plot indicates that the iceball growing speed is less than the ice formation profile 702. In such instances, the cryoablation computing device 102 may increase or otherwise adjust the flow of the cryo-fluid to increase ice growth. At portion 708, the iceball growth may be faster than the linear ice formation profile 702 once again. The cryoablation computing device 102 may again adjust the flow of cryo-fluid to attempt to obtain a growth profile closer to the ice formation profile 702.

In some examples, the cryoablation computing device 102 may include a machine learning model or artificial intelligence that can learn over time what aspect of the cryoablation system 200 can be adjusted and/or what aspects or operating parameters of the cryo-fluid flow best maintain or achieve the desired iceball characteristics. Such models can be trained using laboratory or experimental data and then be re-trained using clinical data to improve over time.

Figure 8:
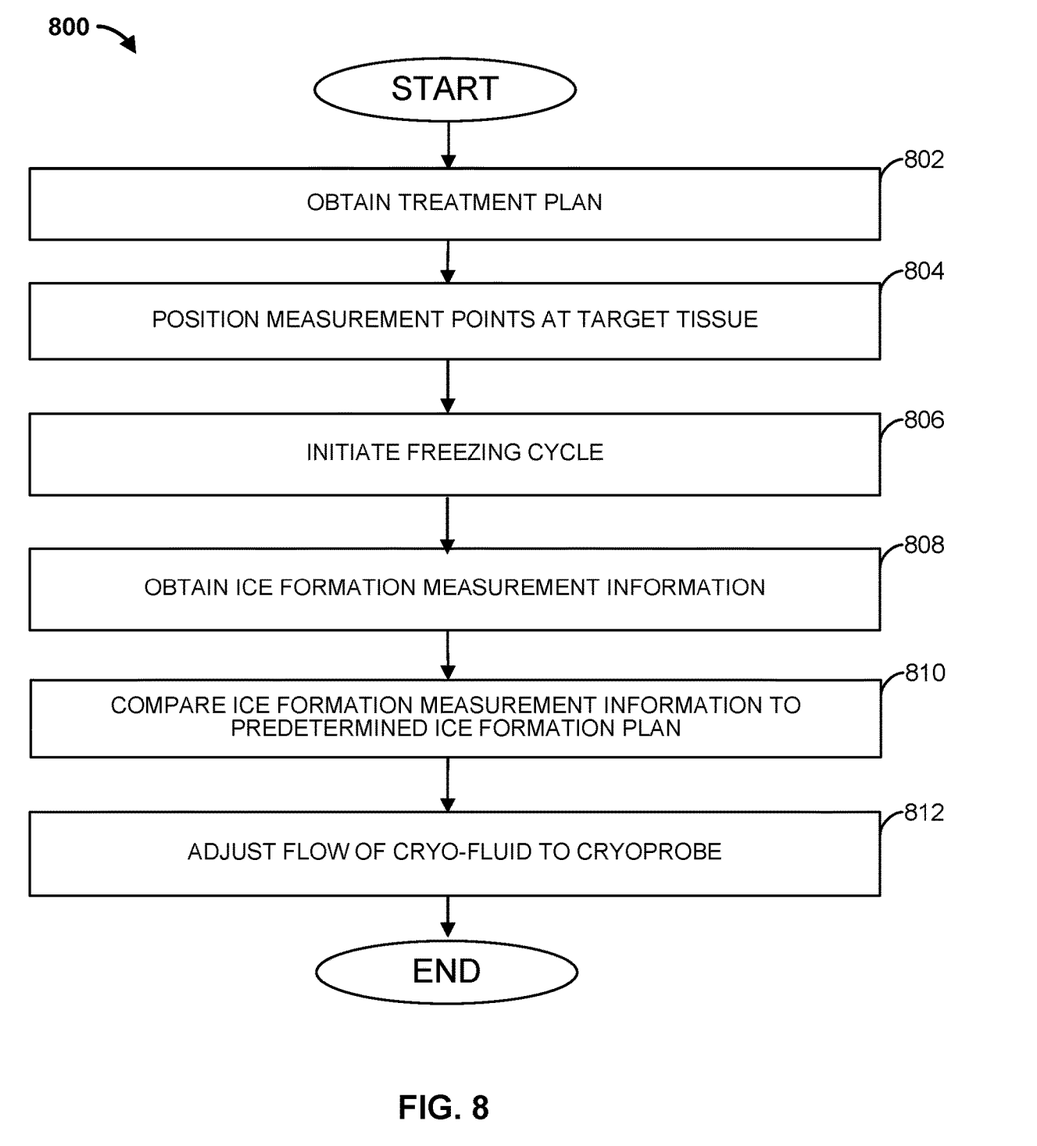
FIG. 8 is a flow chart illustrating another example method of performing a cryoablation treatment in accordance with some embodiments of the present disclosure.

Referring now to FIG. 8, another example method 800 of performing a cryoablation treatment is shown. The method 800 can be performing using any one of the cryoablation systems described herein, such as cryoablation systems 100, 200 and 300. For the sake of brevity, the method 800 is described with reference to the cryoablation system 200 but other cryoablation system can also be used.

At step 802, the cryoablation computing device 102 may obtain a treatment plan. The treatment plan can be obtained from a database, health information system, or other repository. In other examples, the treatment plan may be input into the cryoablation computing device 102 by a user or medical professional using a user interface. The treatment plan may include various aspects that describe details of the cryoablation treatment such as an ice formation plan. The ice formation plan can describe a location, size, shape and other information regarding an iceball that is to be formed during the treatment. The ice formation plan may also include measurement thresholds, ranges or profiles that can be used by the cryoablation computing device 102 to determine whether particular requirements have been achieved during the treatment.

At step 804, the measurement points can be positioned relative to a target tissue. The measurement points may be included on the cryoprobe or may be included on a measurement lead. In some examples, measurement points on both a cryoprobe and on a measurement lead may be used. The cryoprobe and/or the measurement lead can be positioned relative to the target tissue by a medical professional or via a robotic guidance tool. Imaging data may be used in connection with step 804 to verify the positioning of the measurement points relative to the target tissue.

At step 806, the cryoablation computing device 102 may initiate the freezing cycle. As step 806, the cryoablation computing device 102 may instruct the pump 204 to begin providing the cryo-fluid to the cryoprobe 208. As a result, ice may begin to form at the target tissue.

At step 808, the cryoablation computing device 102 may obtain ice formation measurement information. The ice formation measurement information can be obtained from the measurement points. The ice formation measurement information may include, for example, temperature, impedance and other information.

At step 810, the cryoablation computing device 102 may compare the ice formation measurement information to the ice formation plan. The cryoablation computing device 102 may compare the ice formation measurement information to predetermined thresholds, to predetermined ranges and/or to predetermined profiles.

At step 812, the cryoablation computing device 102 may adjust the flow cryo-fluid based on the comparison performed at step 810. If the ice formation measurement information deviates from a predetermined threshold, range or profile by more than a predetermined deviation value, the cryoablation computing device 102 can adjust the flow of cryo-fluid via the pump control 202 and/or the pump 204. In some examples, the cryoablation computing device 102 may adjust a flow speed or a flow volume. In other examples, the cryoablation computing device 102 may adjust a pulse width, a pulse amplitude or pulse frequency of the cryo-fluid flow. In still other examples, the cryoablation computing device 102 may adjust other operating conditions or parameters of the cryoablation system 200.

The steps 808 through 812 may be re-performed continuously, semi-continuously or periodically to monitor and adjust the cryoablation system 200 during a treatment. This monitoring loop may be performed until one or more predetermined ice formation requirements are achieved during the treatment. The ice formation requirements may include an ice size, shape, temperature and/or duration. Once achieved, the method 800 may end.

Figure 9:
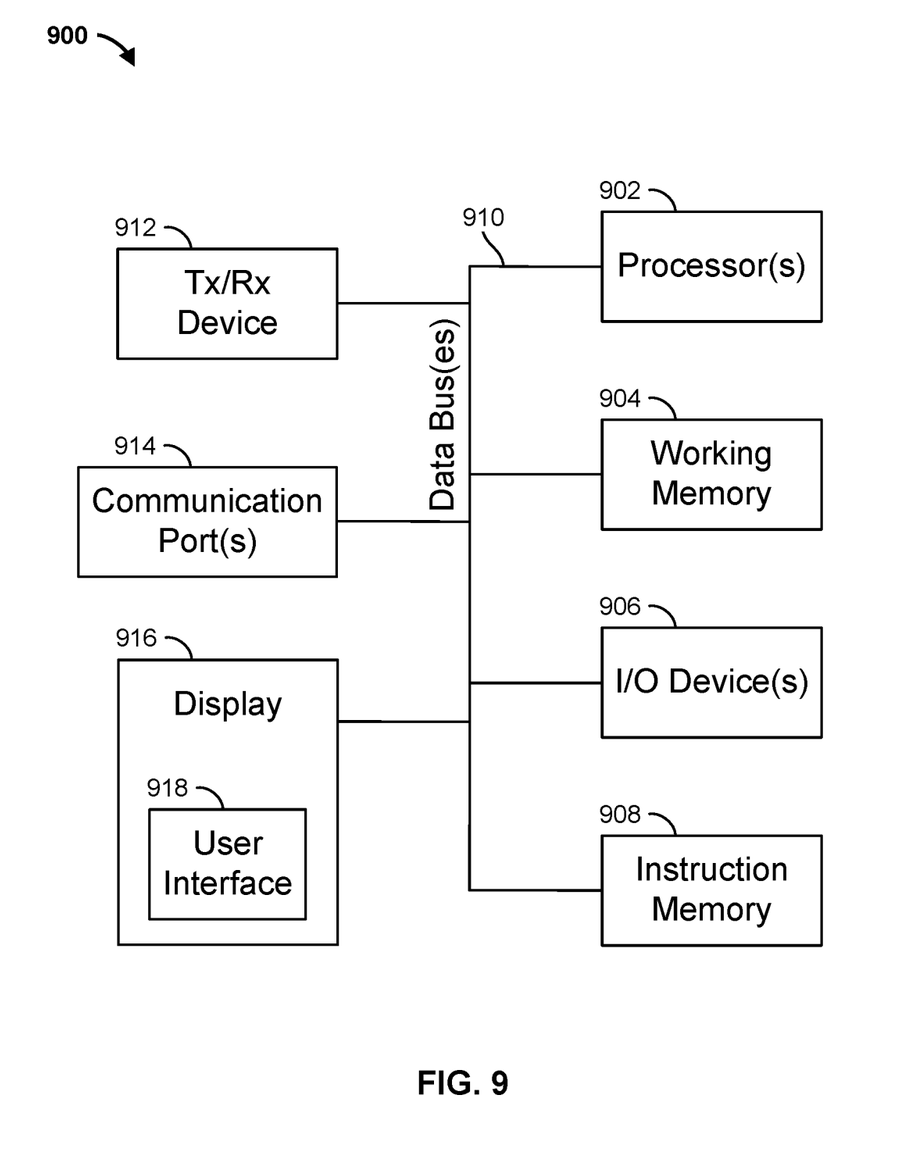
FIG. 9 is a diagram illustrating an example computing device that can be used in one or more cryoablation systems of the present disclosure.

Referring now to FIG. 9, an example computing device 900 is shown. The cryoablation system 100, 200 or 300 may include one or more computing devices 900. For example, the cryoablation computing device 102 may have the elements shown in FIG. 8. The methods of the present disclosure, such as methods 400, 500, and 800, may be performed, or steps of such methods may be performed, by a computing device 900.

As shown, the computing device 900 may include one or more processors 902, working memory 904, one or more input/output devices 906, instruction memory 908, a transceiver 912, one or more communication ports 914, and a display 916, all operatively coupled to one or more data buses 910. Data buses 910 allow for communication among the various devices. Data buses 910 can include wired, or wireless, communication channels.

Processors 902 can include one or more distinct processors, each having one or more cores. Each of the distinct processors can have the same or different structure. Processors 902 can include one or more central processing units (CPUs), one or more graphics processing units (GPUs), application specific integrated circuits (ASICs), digital signal processors (DSPs), and the like.

Processors 902 can be configured to perform a certain function or operation by executing code, stored on instruction memory 908, embodying the function or operation. For example, processors 902 can be configured to perform one or more of any function, step, method, or operation disclosed herein.

Instruction memory 908 can store instructions that can be accessed (e.g., read) and executed by processors 902. For example, instruction memory 908 can be a non-transitory, computer-readable storage medium such as a read-only memory (ROM), an electrically erasable programmable read-only memory (EEPROM), flash memory, a removable disk, CD-ROM, any non-volatile memory, or any other suitable memory.

Processors 902 can store data to, and read data from, working memory 904. For example, processors 902 can store a working set of instructions to working memory 904, such as instructions loaded from instruction memory 908. Processors 902 can also use working memory 904 to store dynamic data created during the operation of cryoablation computing device 102. Working memory 904 can be a random access memory (RAM) such as a static random access memory (SRAM) or dynamic random access memory (DRAM), or any other suitable memory.

Input-output devices 906 can include any suitable device that allows for data input or output. For example, input-output devices 906 can include one or more of a keyboard, a touchpad, a mouse, a stylus, a touchscreen, a physical button, a speaker, a microphone, or any other suitable input or output device.

Communication port(s) 914 can include, for example, a serial port such as a universal asynchronous receiver/transmitter (UART) connection, a Universal Serial Bus (USB) connection, or any other suitable communication port or connection. In some examples, communication port(s) 914 allows for the programming of executable instructions in instruction memory 908. In some examples, communication port(s) 914 allow for the transfer (e.g., uploading or downloading) of data, such as ice formation measurement data and the like.

Display 916 can display a user interface 918. User interfaces 918 can enable user interaction with the cryoablation computing device 102. For example, user interface 818 can be a user interface that allows an operator to interact, communicate, control and/or modify different messages, settings, or features that may be presented or otherwise displayed to a user. The user interface 918 can include a slider bar, dialogue box, or other input field that allows the user to control, communicate or modify a setting, limitation or input that is used in a cryoablation treatment. In addition, the user interface 918 can include one or more input fields or controls that allow a user to modify or control optional features or customizable aspects of the cryoablation computing device 102 and/or the operating parameters of the cryoablation system 100, 200 or 300. In some examples, a user can interact with user interface 918 by engaging input-output devices 906. In some examples, display 916 can be a touchscreen, where user interface 918 is displayed on the touchscreen. In other examples, display 916 can be a computer display that can be interacted with using a mouse or keyboard.

Transceiver 912 allows for communication with a network. In some examples, transceiver 912 is selected based on the type of communication network cryoablation computing device 102 will be operating in. Processor(s) 902 is operable to receive data from, or send data to, a network, such as wired or wireless network that couples the elements of the cryoablation system 100, 200 or 300.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for performing a cryoablation treatment comprising at least one computing device, the at least one computing device configured to:
   obtain ice formation measurement information from a plurality of measurement points, the plurality of measurement points positioned at predetermined locations relative to a target tissue in a patient;
   determine a rate of change of a temperature at each measurement point of the plurality of measurement points based on the ice formation measurement information;
   compare the ice formation measurement information to a predetermined ice formation plan by comparing the rate of change of the temperature at each measurement point of the plurality of measurement points to a rate of change in the predetermined ice formation plan; and
   adjust a flow of a cryo-fluid to a cryoprobe if the ice formation measurement information deviates from the predetermined ice formation plan by more than a predetermined deviation level.

2. The system of claim 1, wherein the plurality of measurement points are positioned on the cryoprobe.

3. The system of claim 1, wherein the plurality of measurement points are positioned on a measurement lead separate from the cryoprobe, the measurement lead positioned in a desired orientation relative to the cryoprobe.

4. The system of claim 3, wherein the measurement lead comprises a linear shape extending away from the cryoprobe in a longitudinal direction such that the orthogonal distance of the measurement lead from the cryoprobe increases in a direction away from a tip of the cryoprobe.

5. The system of claim 1, wherein the plurality of measurement points are positioned on both the cryoprobe and a measurement lead separate from the cryoprobe.

6. The system of claim 1, wherein the ice formation measurement information comprises temperatures at the plurality of measurement points, and the at least one computing device compares the temperatures to temperature thresholds.

7. The system of claim 1, wherein the at least one computing device is configured to adjust at least one of a flow speed or a flow volume of the cryo-fluid flow.

8. The system of claim 1, wherein the at least one computing device is configured to adjust at least one of a pulse width, a pulse amplitude or pulse frequency of the cryo-fluid flow.

9. The system of claim 1, wherein the at least one computing device is configured to continuously obtain the ice formation measurement information and continuously adjust the flow of the cryo-fluid to the cryoprobe if the ice formation measurement information deviates from the predetermined ice formation plan until the ice formation measurement information that a desired ice formation has been achieved for predetermined freezing time.

10. The system of claim 1, further comprising a pump fluidly connected to a cryo-fluid source and a cryo-fluid supply line, the at least one computing device configured to adjust the flow of the cryo-fluid to the cryoprobe using the pump.

11. A method of performing a cryoablation treatment comprising:
  positioning a plurality of measurement points in predetermined locations relative to a target tissue in a patient;
  determining a rate of change of a temperature at each measurement point of the plurality of measurement points based on the ice formation measurement information;
  obtaining ice formation measurement information from the plurality of measurement points;
  comparing the ice formation measurement information to a predetermined ice formation plan by comparing the rate of change of the temperature at each measurement point of the plurality of measurement points to a rate of change in the predetermined ice formation plan; and
  adjusting a flow of a cryo-fluid to a cryoprobe if the ice formation measurement information deviates from the predetermined ice formation plan by more than a predetermined deviation level.

12. The method of claim 11, wherein the plurality of measurement points are located on the cryoprobe.

13. The method of claim 11, wherein the plurality of measurement points are located on a measurement lead separate from the cryoprobe, the measurement lead positioned in a desired orientation relative to the cryoprobe.

14. The method of claim 13, wherein the measurement lead comprises a linear shape extending away from the cryoprobe in a longitudinal direction such that the orthogonal distance of the measurement lead from the cryoprobe increases in a direction away from a tip of the cryoprobe.

15. The method of claim 11, wherein the plurality of measurement points are located on the cryoprobe and a measurement lead separate from the cryoprobe.

16. The method of claim 11, wherein the ice formation measurement information comprises temperatures at the plurality of measurement points, and the temperatures are compared to temperature thresholds.

17. The method of claim 11, wherein the step of adjusting the flow of the cryo-fluid comprises adjusting at least one of a flow speed and a flow volume.

18. The method of claim 11, wherein the step of adjusting the flow of the cryo-fluid comprises adjusting at least one of a pulse width, a pulse amplitude or pulse frequency of the cryo-fluid flow.

19. The method of claim 11, further comprising continuously obtaining the ice formation measurement information and continuously adjusting the flow of the cryo-fluid to the cryoprobe if the ice formation measurement information deviates from the predetermined ice formation plan until the ice formation measurement information that a desired ice formation has been achieved for predetermined freezing time.

20. The method of claim 11, wherein the step of adjusting the flow of the cryo-fluid is automatically performed by the at least one computing device coupled to pump that is fluidly connected to a cryo-fluid source and a cryo-fluid supply line.

* * * * *